US00PP34177P2

(12) United States Plant Patent
Holtmaat

(10) Patent No.: US PP34,177 P2
(45) Date of Patent: Apr. 26, 2022

(54) ***HEUCHERA* PLANT NAMED 'REX BLACK'**

(50) Latin Name: ***Heuchera* hybrid**
Varietal Denomination: Rex Black

(71) Applicant: Henricus Maria Joseph Holtmaat, Zuidwolde (NL)

(72) Inventor: Henricus Maria Joseph Holtmaat, Zuidwolde (NL)

(73) Assignee: AB-KWEKERSRECHTEN B.V., Zuidwolde (NL)

( * ) Notice: Subject to any disclaimer, the term of this patent is extended or adjusted under 35 U.S.C. 154(b) by 0 days.

(21) Appl. No.: 17/468,359

(22) Filed: Sep. 7, 2021

(51) Int. Cl.
*A01H 5/12* (2018.01)
*A01H 6/80* (2018.01)

(52) U.S. Cl.
USPC ..... Plt./440
CPC ..... *A01H 6/80* (2018.05)

(58) Field of Classification Search
USPC ..... Plt./440
CPC ..... A01H 6/80
See application file for complete search history.

*Primary Examiner* — Anne Marie Grunberg
(74) *Attorney, Agent, or Firm* — Penny J. Aguirre

(57) ABSTRACT

A new cultivar of *Heuchera* plant named 'Rex Black' that is characterized by its conspicuous large leaves, its foliage that is blackish in color, its strong and sturdy plant habit, and its flowers that are light lilac-pink in color.

3 Drawing Sheets

Botanical classification: *Heuchera* hybrid.
Cultivar designation: 'Rex Black'.

BACKGROUND OF THE INVENTION

The present invention relates to a new and distinct cultivar of *Heuchera* of hybrid origin, botanically known as *Heuchera* 'Rex Black' and is hereinafter referred to by its cultivar name 'Rex Black'.

The new cultivar was discovered as a chance seedling in a container by the Inventor in Zuidwolde, The Netherlands in June of 2019. The source of the seedling was from seed collected in 2019 from open pollinated plants in a trial field that contained numerous unnamed and unpatented proprietary *Heuchera* seedlings from the Inventor's breeding program. The parentage of 'Rex Black' is therefore unknown.

Asexual propagation of the new cultivar was first accomplished under the direction of the Inventor by tissue culture initiated from meristem tissue in April of 2020 in Heerhugowaard, The Netherlands. Asexual propagation of the new cultivar by tissue culture has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Rex Black' as a new and unique cultivar of *Heuchera*.

1. 'Rex Black' exhibits conspicuous large leaves.
2. 'Rex Black' exhibits foliage that is blackish in color.
3. 'Rex Black' exhibits a strong and sturdy plant habit.
4. 'Rex Black' exhibits flowers that are light lilac-pink in color.

'Rex Black' can be most closely compared to the *Heuchera* cultivars 'Black Pearl' (U.S. Plant Pat. No. 29,395) and 'Rex Purple' (U.S. Plant Pat. No. 30,443). 'Black Pearl' is similar to 'Rex Black' in foliage color. 'Black Pearl' differs from 'Rex Black' in having a lower growing habit and leaves that are smaller in size. 'Rex Purple' is similar to 'Rex Black' in plant height and leaf size. 'Rex Purple' differs from 'Rex Black' in having a foliage that is lighter and more purple in color and flowers that are light pinkish white in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but are not limited to website disclosures by the Polish Nurseryman Association, Dobrepole, Podoslonami, Zielony Ogrodek, and Flamingo Holland Inc (Vitroflora).

BRIEF DESCRIPTION OF THE DRAWINGS

The accompanying color photographs illustrate the overall appearance and distinct characteristics of the new *Heuchera*. The photographs were taken of a plant 18 months in age of the new cultivar as grown outdoors in 19-cm containers Zuidwolde, The Netherlands.

The photograph in FIG. 1 provides a side view of the plant of 'Rex Black' in bloom.

Figure 1:
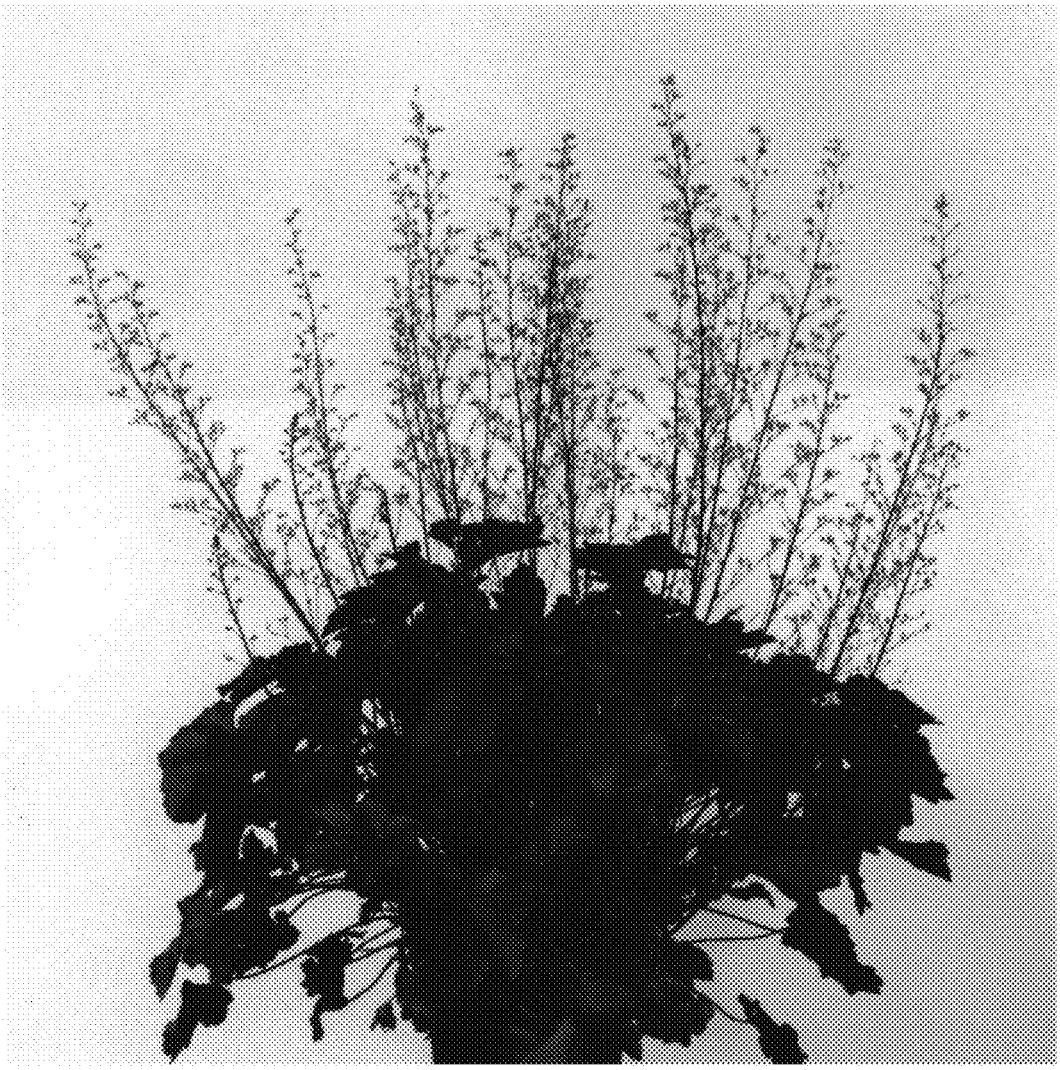
Figure 2:
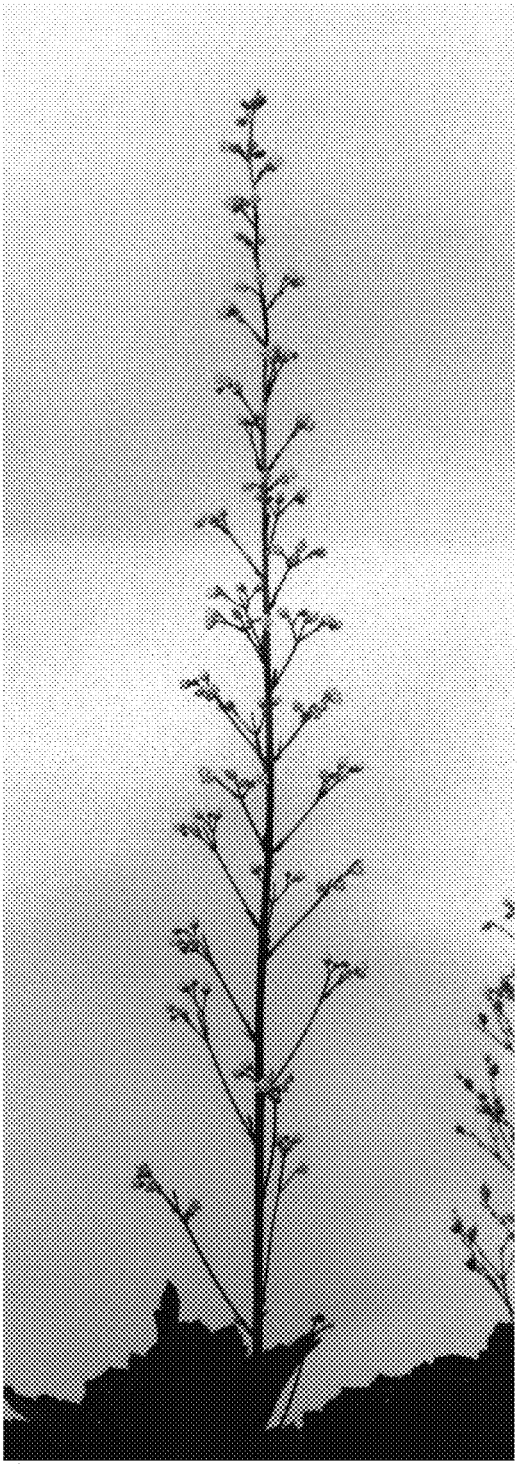

The photograph in FIG. 2 provides a close up of an inflorescence of 'Rex Black'.

Figure 3:
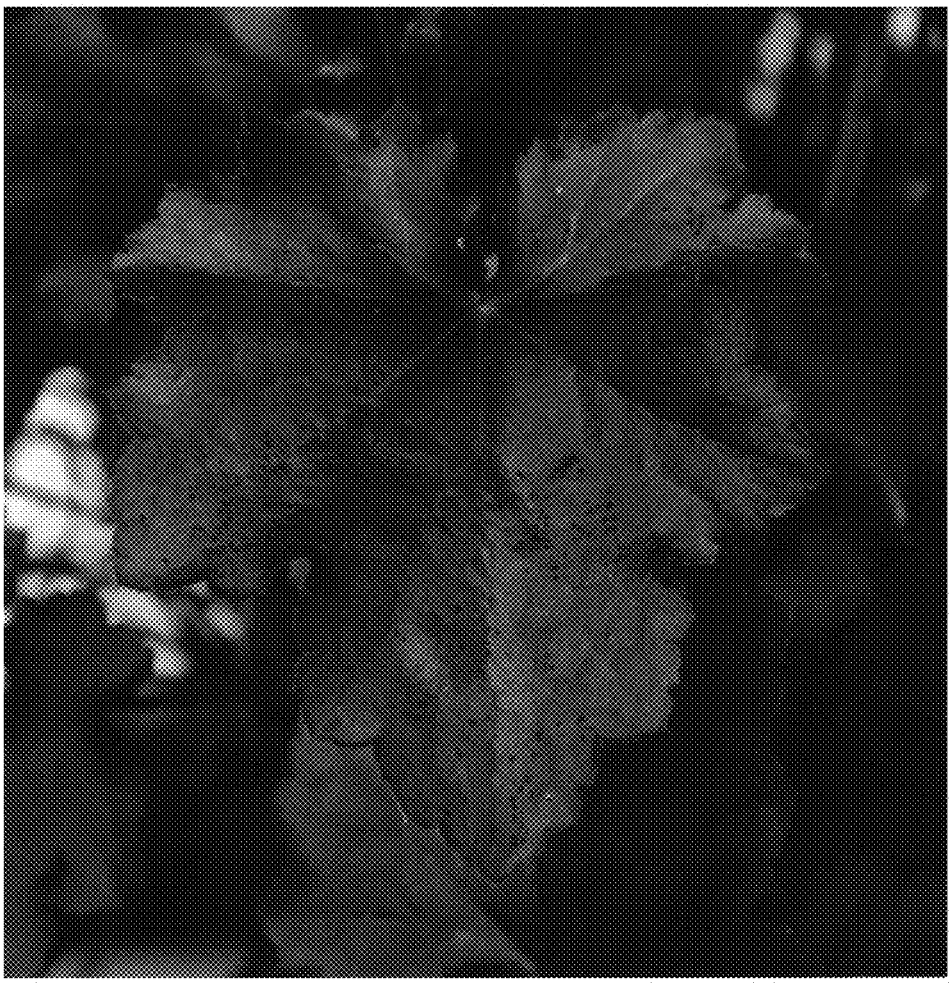

The photograph in FIG. 3 provides a close up view of the foliage of 'Rex Black'.

The colors in the photographs are as close as possible with the digital photography techniques available, the color values cited in the detailed botanical description accurately describe the colors of the new *Heuchera*.

DETAILED BOTANICAL DESCRIPTION OF THE PLANT

The following is a detailed description of 18 month-old plants of the new cultivar as grown outdoors in 19-cm containers Zuidwolde, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—8 weeks in midsummer in The Netherlands.

*Plant type*.—Herbaceous perennial.

*Plant habit*.—Flattened globular with inflorescences held above the foliage.

*Height and spread*.—An average of 44.5 cm in height (soil level to top of foliar plane), average of 92 cm in height (soil level to top of floral plane) and 92 cm in spread.

*Cold hardiness*.—At least in U.S.D.A. Zone 3.

*Diseases and pests*.—No susceptibility or resistance to pests or diseases has been observed.

*Root description*.—Fibrous roots on woody rootstalks, 158D in color.

*Propagation*.—Tissue culture.

*Root development*.—An average of 3 weeks for root initiation, 6 weeks to produce a rooted cutting.

*Growth rate*.—Vigorous.

*Stem number*.—Average of 27 basal rosettes.

*Branching habit*.—Flowering stems emerge from basal rosette, an average of 27 rosettes per plant, no lateral branches.

Foliage description:

*Leaf shape*.—Nearly orbicular in outline, very slightly concave.

*Leaf division*.—Simple.

*Leaf base*.—Hastate, lobes free.

*Leaf apex*.—Short and abruptly acute.

*Leaf venation*.—Laciniate, upper surface 200C, lower surface 187A.

*Leaf margins*.—Crenate with abruptly acute tips on each tooth, slightly to moderately coarsely undulate.

*Leaf attachment*.—Petiolate.

*Leaf arrangement*.—Alternate in basal rosettes.

*Leaf lobes*.—Lobed, an average of 7 to 9 lobes, occasionally 11, shallow to medium in depth, divergent, lobe margins free.

*Leaf surface*.—Upper surface smooth and moderately velvety, lower surface smooth, both surfaces moderately to densely covered with very short strigose hairs upper surface hairs; an average of 0.5 mm in length and too small to measure color, lower surface hairs an average of 1 mm in length, 156D in color.

*Leaf color*.—Young upper surface; a blend of 200A and 200B, young lower surface; a blend of N79B and 187B, mature upper surface; 203A, becoming tinged with 147B when maturing later in summer and early fall, mature lower surface; a blend of N79A and N186C, changing to a blend of N186C and 187A in late summer and early fall.

*Leaf size*.—An average of 13.6 cm in length and 13.2 cm in width.

*Leaf quantity*.—An average of 8 per basal rosette.

*Petioles*.—An average of 24 cm in length and 3.5 mm in diameter, moderate strength, both surfaces glossy, upper surface color N186C, lower surface color 200B, tinged N186C, very densely covered with short, soft strigose hairs an average of 1.5 mm in length, 156D in color.

*Stipules*.—Leafy stipule at the base of each leaf, average 2 cm in length, average 5 mm in width, acute tip, 187A in color.

Flower description:

*Inflorescence type*.—Numerous small bell-shaped flowers arranged on panicles on peduncles emerging from a basal rosette.

*Inflorescence size*.—An average of 51.9 cm in height and 10.3 cm in diameter.

*Inflorescence number*.—An average of 30.

*Density of flowers per inflorescence*.—Medium.

*Flower fragrance*.—None.

*Flower quantity*.—Average of 225 flowers per flowering stem, 2,000 per plant.

*Flower lastingness*.—Average of one week.

*Flower buds*.—Obovate in shape, an average of 3 mm in length and 2.25 mm in diameter, color; 184C, lower half 186A, surface is matte and densely covered with very short glandular hairs; an average of 0.2 mm in length and too small to measure color.

*Flower aspect*.—Nodding to held slightly outward.

*Flower type*.—Single, campanulate.

*Flower size*.—Average of 6 mm in height and diameter, 7 mm in length.

*Petals*.—Average of 5, rotate arrangement and implanted in the hypanthium at base, oblanceolate in shape, margin is entire, apex is acute, base is narrow attenuate, upper and lower surface is glabrous, smooth and matte, an average of 3.5 cm in length and 0.5 mm in width, color when opening and fully open upper and lower surface; 76D.

*Calyx*.—Campanulate, sepals fused to hypanthium, 4 mm in length and diameter.

*Sepals*.—An average of 5, lower 50% fused into campanulate hypanthium, short oblong in shape, an average of 4 mm in length and 1.5 mm in width, margin is entire and fused into hypanthium, apex is obtuse, color; when opening and fully open upper surface 76A, margins 76D, tips 147A, lower half 186A, when opening and fully open lower surface 75C, towards the top N74A, tip 147A, lower half 186A, both surfaces are matte and densely covered with very short glandular hairs an average of 0.2 mm in length and to small to measure color.

*Peduncle*.—An average of 76 cm in length and 3 mm in diameter, color; 200A, proximal end N199A and N199B, primary flower aspect 60°, secondary peduncle aspect to main peduncle 35°, moderate in strength, surface moderately glossy and densely covered with very short soft glandular hairs; average of 0.5 mm in length, NN155D in color.

*Pedicels*.—An average of 4 mm in length and 0.5 mm in diameter, 200A in color, primary flower aspect straight on top of secondary pedicel, secondary and tertiary flower aspect is 50°, moderate in strength, surface matte and densely covered with very short soft glandular hairs; average of 0.2 mm in length and too small to measure color.

Reproductive organs:

*Gynoecium*.—Pistils; 2, 4.5 mm in length, stigma; club-shaped, 0.2 mm in diameter, style; an average of 4.25 mm in length and 76D in color, ovary; 146D in color.

*Androecium*.—Stamens; 5, anthers; ovate in shape, average of 0.3 mm in length and width, N199A in color, filament; 2 mm in length and N155B in color, pollen; low in quantity and too little to measure color.

*Seed/fruit*.—No fruit or seeds have been observed to date.

It is claimed:

1. A new and distinct cultivar of *Heuchera* plant named 'Rex Black' as herein illustrated and described.

* * * * *